United States Patent [19]

Riggi

[11] 3,933,156

[45] Jan. 20, 1976

[54] COOLING APPARATUS PARTICULARLY FOR MEDICAL-SURGICAL USE

[76] Inventor: Giovanni Riggi, Via Giacosa 2 bis, Turin, Italy

[22] Filed: Jan. 8, 1975

[21] Appl. No.: 539,564

[30] Foreign Application Priority Data

Jan. 15, 1974 Italy .................................. 67108/74

[52] U.S. Cl. ............................................ 128/303.1
[51] Int. Cl.² ......................................... A61B 17/36
[58] Field of Search ............ 128/303.1, 400; 62/293

[56] References Cited
UNITED STATES PATENTS

| | | | |
|---|---|---|---|
| 3,712,306 | 1/1973 | Bryne | 128/303.1 |
| 3,794,039 | 2/1974 | Kollner et al. | 128/303.1 |
| 3,807,403 | 4/1974 | Stumpf et al. | 128/303.1 |

*Primary Examiner*—Lawrence W. Trapp
*Attorney, Agent, or Firm*—Sughrue, Rothwell, Mion, Zinn & Macpeak

[57] ABSTRACT

Refrigerating apparatus for medical use including a probe comprising two concentric tubes through the inner tube of which, in use of the apparatus, a refrigerant is forced so as to expand into the outer tube as it leaves the inner tube thereby refrigerating the tip of the probe by flash evaporation and expansion, then flowing back along the space between the tubes, in which there are provided two further tubes surrounding the probe except for the refrigerating tip and defining passageways between themselves and the outer tube through which the refrigerant is fed before being introduced into the innermost tube, to provide thermal insulation for the sides of the probe apart from the refrigerating tip.

3 Claims, 2 Drawing Figures

COOLING APPARATUS PARTICULARLY FOR MEDICAL-SURGICAL USE

BACKGROUND OF THE INVENTION

The present invention relates to refrigerating apparatus, and particularly to refrigerating apparatus for medical use. Such refrigerating apparatus, which may be used for surgical or therapeutic use, comprises a tubular probe within which is a capillary tube along which, in use of the apparatus, flows a refrigerant fluid which evaporates at a temperature lower than room temperature, which fluid is supplied to the capillary tube in the liquid state; the refrigerant is drawn in the gaseous state from a pressurised container and flows through a thermostatic condenser by which it is liquified before it is fed to the capillary tube within the probe. The end of the capillary tube communicates with an expansion chamber at the tip of the probe and flash evaporation and expansion of the refrigerant fluid as it flows from the capillary tube into the expansion chamber causes refrigeration of the walls of the expansion chamber. The refrigerant fluid then flows back from the expansion chamber along an annular conduit between the capillary tube and a second tube which surrounds it. From the annular conduit the refrigerant flows through a valve controllable by the operator and escapes to the atmosphere.

Refrigerating apparatus of this type, which is used medically to locally freeze body tissue for therapeutic and/or surgical purposes is often referred to as a cryosurgical or cryotherapeutical insturment. Such instruments have been successfully in use for some years, mostly in the fields of gynaecology, otorhinolaryngology, dermatology and ophthalmology.

One disadvantage of known medical refrigerating instruments, however, is the difficulty of providing satisfactory thermal insulation of the refrigerated tip of the probe from the remainder of the probe. In known cryosurgical instruments the whole of the probe and even the operator's hand grip can become extremely cold, and the temperature of the probe can approach that of the refrigerating tip after long periods of continuous use.

When treating skin, the fact that the probe is at a low temperature along the whole of its length does not cause serious difficulty and when the instrument is employed in fairly wide body cavities the probe can be provided with a thermal insulating covering along its length, except for the refrigerating tip, which results in an increase in cross-sectional size of the probe.

However, for use in narrowly restricted body regions, which is necessary, for example, in the ophthalmic field when operating on the retina, an increase in cross-sectional size of the probe is inadmissible, rather this size should be reduced as far as possible. If the probe is not well insulated along its length, however, the danger arises that the sides of the probe could accidentally touch parts which are not to be refrigerated and injure them irreparably. It is therefore clear that the use of a refrigerating instrument without insulated probes for eye operations requires a very high degree of skill by the surgeon.

OBJECT AND SUMMARY OF THE INVENTION

The object of the invention is to provide a medical refrigerating instrument in which the temperature of the probe walls, except for the operating region of the tip actually to be refrigerated, is kept at a temperature which is not injurious to body tissue during operation of the instrument.

According to the present invention, there is provided refrigeration apparatus suitable for medical use, of the type having a tubular probe carried at one end in a mounting body and being free at the other end, the probe comprising first and second concentric tubes, the first tube being positioned within the second tube and being formed as a capillary tube through which, in use of the apparatus, a refrigerant fluid which evaporates at a temperature below room temperature, is caused to flow in the liquid state from one end of the probe to the other, the second tube being closed at the said other end of the probe and surrounding the said other end of the first tube to form an expansion chamber into which, in operation of the apparatus, the refrigerant fluid expands upon discharge from the said other end of the first tube, to refrigerate an outer wall of said chamber by flash evaporation, the refrigerant fluid in a gaseous state then flowing along the annular passageway between the first and second tubes and being discharged to the atmosphere through a discharge valve operable by the operator, in which the second tube is surrounded by a third tube which is co-axial therewith and spaced therefrom to define a second annular passageway between said second and third tubes, and said third tube is surrounded in turn by a fourth tube which is spaced therefrom to define a third annular passageway, the second and third annular passageways communicating with each other at the said other end of the probe but not communicating with said expansion chamber, and the third and fourth tubes of such a length as to partly surround the expansion chamber leaving a part only thereof exposed, the second and third annular passageways being connected in series in the flow path of the refrigerant fluid between a source thereof and the said one end of the first tube so that, in use of the apparatus, the refrigerant fluid flowing therethrough serves as thermal insulation for the first and second tubes of the probe, which tubes are in thermal contact with the expansion chamber.

In one embodiment of the invention the mounting body which carries the probe is adapted to support a container of refrigerant fluid which serves as a handle by means of which the apparatus can be hand held, the mounting body also carrying a condenser coil and being formed with internal conduits linking the refrigerant fluid container to one end of the third annular passageway on the probe, one end of the second annular passageway of the probe to one end of the condenser coil, the other end of the condenser coil to the said one end of the first tube, and the said one end of the first annular passageway to the discharge valve.

The present invention also comprehends a tubular probe for refrigerating apparatus such as refrigerating apparatus for medical use, comprising a first tube formed as a capillary tube for a refrigerant in the liquid state which, in use of the probe, is passed through the central bore of the tube from one end to the other, a second tube coaxial with and surrounding the first tube to define therewith an annular passageway, the second tube extending past the said other end of the first tube and being closed to form an expansion chamber into which refrigerant fluid can expand as it leaves the said other end of the first tube, the second tube being surrounded by a third tube which defines therewith a second annular passageway and the third tube being surrounded by a fourth tube which defines therewith a third annular passageway, the second and third annular passageways communicating with each other adjacent the said other end of the first tube but being separated from the said expansion chamber, and the said third and fourth tubes being of such a length as to partly surround the expansion chamber leaving a part only thereof exposed.

The invention thus provides a solution to the problem of thermal insulation of the probe of such refrigeration apparatus without excessively increasing the outer diameter of the probe. Although four concentric tubes are used the size can nevertheless be kept small since tubes are presently available in which the wall thickness is only a few tenths of a millimeter. Such tubes make it possible for the annular passageways between adjacent tubes to be wide enough for satisfactory operation without requiring the outermost tube to be more than a few millimeters in diameter.

A further advantage of the invention is the possibility of providing a fully self-contained refrigerating instrument in which the source of refrigerant fluid is a container holding the refrigerant in liquid form under pressure, the container doing double duty as a hand grip. This arrangement has advantages in that it exploits the heat of the operator's hand holding the container for use without requiring any additional devices such as an electrical resistance heater for warming the refrigerant in the container. Embodiments of the invention have advantages over known such refrigeration apparatus, even if the probe is not required to be of a very small cross-section, in circumstances, including nonmedical uses, where refrigeration is required only in an accurately defined localized area, while refrigeration of adjacent regions, is to be avoided.

Further features and advantages of the invention will become apparent from a consideration of the following description with reference to the accompanying drawings, which is provided purely by way of non-restrictive example.

DESCRIPTION OF THE PREFERRED EMBODIMENT

Figure 1:
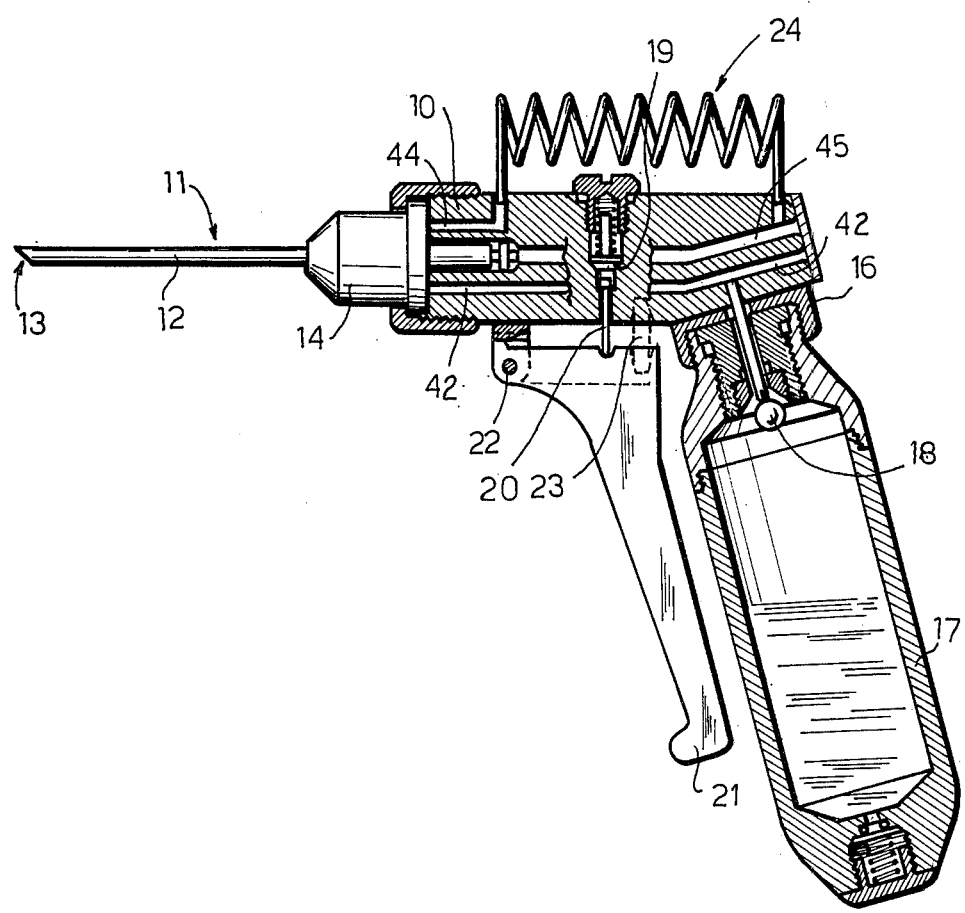
FIG. 1 is a longitudinal cross-sectional view of a self-contained pistol-shaped refrigerating instrument according to this invention.

Referring now to FIG. 1, the instrument comprises a body portion 10 which may be made of chromeplated brass, having secured to its forward end a tubular probe 11 which includes a tubular portion 12 projecting from a socket 14 which is held on to the body portion 10 by means of a threaded ring 15. The socket 14 is formed internally with a plurality of conduits for connection with cooperating conduits in the body portion 10. The distal end 13 of the tubular portion 12 of the probe 13 is formed as a refrigerating tip.

The rear portion of the body 10 is provided with an internally threaded coupling 16 for attachment of a bottle or flask 17 which also serves as a handle. The flask 17 contains a suitable refrigerant, such as nitrous oxide, carbon dioxide or the refrigerant sold under the trade name "Freon", at such a pressure that it is held in a liquid condition at room temperature. As shown, the flask 17 is provided with a conventional ball-valve 18 which is opened by a probe on the body portion when the flask 17 is screwed onto the coupling 16.

The body 10 is further provided with a poppet valve 19 biased to the closed position by a spring, and openable via a push rod 20, by a trigger 21 pivotally mounted on the body portion 10 by a pivot 22 and biased by a spring 23. The size and arrangement of the flask 17 and the trigger 21 is such that when the flask is held in the hand the trigger can be easily reached by the fingers and operated to open the poppet valve 19 by drawing it towards the flask 17.

The upper portion of the body 10 is provided with a thermostatic condenser 24 comprising a tubular coil, such as of stainless steel.

Figure 2:
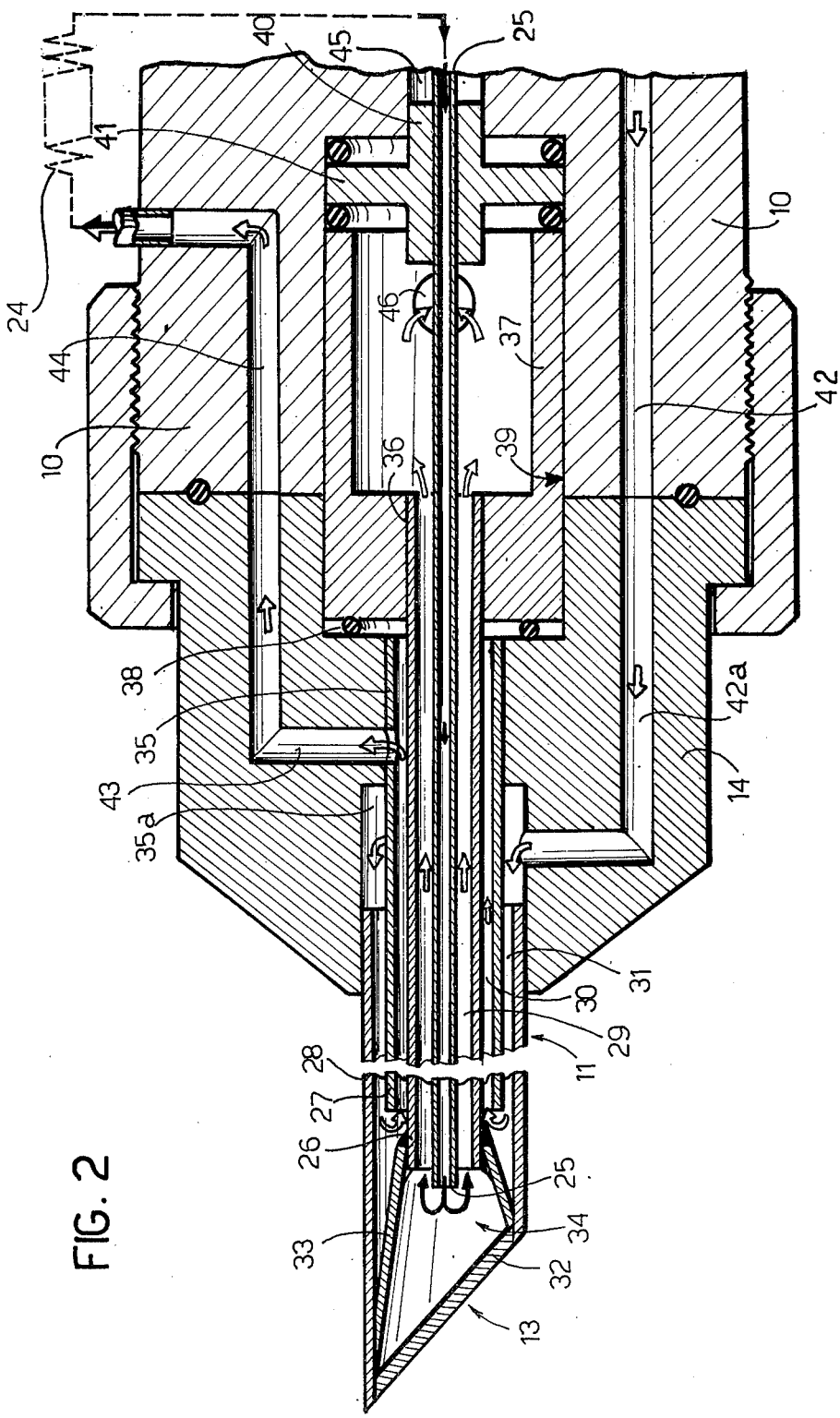
FIG. 2 is a longitudinal cross-sectional view on an enlarged scale showing the probe of the instrument shown in FIG. 1, and part of the body of the instrument to which it is secured.

Referring to FIG. 2, the tubular portion of the probe 11 comprises four concentric tubes 25, 26, 27 and 28, the tube 25 being the innermost and the tube 28 being the outermost. The innermost tube 25 is sufficiently narrow to serve as a capillary tube for the refrigerant in the liquid state, and the tubes 26, 27 and 28 define annular passageways 29, 30 and 31.

The outermost tube 28 is closed at the distal end 13 of the probe by a closure plate 32 which, in the embodiment shown, forms an end face of the probe tip and is inclined obliquely to the axis of the probe 11. Hereinafter the two intermediate tubes 26 and 27 will be referred to as the inner intermediate tube and the outer intermediate tube respectively.

The distal end of the inner intermediate tube 26 is spaced inwardly from the end of the outer tube 28 and is connected thereto by a frustoconical separating element 33. The small end of the frustoconoical separator 33 is sealingly welded to the end of the inner intermediate tube 26, and its large end, which is inclined to correspond in shape to the inclined end of the outer tube 28 is sealingly welded to the inner surface of the end of the outer tube 28 adjacent the plate 32. The outer intermediate tube 27 ends a short distance from the separator 33.

With this arrangement the separator 33 forms the inner wall of an expansion chamber 34 the only exterior wall of which is formed by the end plate 32. The capillary tube 25 communicates with the chamber 24 as does the inner annular passageway 29, but the intermediate and outer annular passageways 30 and 31 are separated from the chamber 34 by the separator 33. The two annular passageways 30 and 31 intercommunicate rearwardly of the separator 33.

The outer intermediate tube 27 and the outer tube 28 are sealingly fixed to the socket 14, in a central bore 35 and a cylindrical recess 35a, respectively, the recess 35a being concentric with the bore 35. The inner intermediate tube 26 is sealingly fixed in a hole 36 in the base of a cup shaped intermediate element 37 which is fitted both into a recess 38 in the socket 14 and into a coaxial cylindrical cavity 39 in the body portion 10. Finally, the capillary tube 25 is sealingly fixed in a sleeve 40 mounted by means of a flange 41 in the cavity 38, behind the intermediate element 37. Suitable O-rings are interposed between the body portion 10 and the socket 14, between the socket 14 and the intermediate element 37, between the element 38 and the flange 41, and between the flange 41 and the body portion 10, to isolate the various chambers and passageways within the body 10 from one another.

The tubes 25, 26, 27 and 28, the plate 32 and separator 33 are preferably made of stainless steel of narrow wall thickness, for example of the order of a few tenths of a millimeter, so that the outer tube 28 can be made of a very small diameter such as 3 mm. Although a straight probe has been shown, the probe could be made of any curved or bent form, and its distal end or tip can be of any desired shape depending upon its intended use.

The flask 17 is directly connected, through aligned conduits 42, 42a bored in the body portion 10 and socket 14, respectively, with the outer annular passageway 31. The intermediate annular passageway 30 is directly connected, through aligned conduits 43, 44 bored in the socket 14, and body portion 10 respectively, to one end of the condenser coil 24 the other end of which is directly connected, through a conduit 45 bored in the body portion 10, with the capillary tibe 25. The inner annular passageway 29 is connected through a conduit, not shown but having its inlet at 46, with the discharge valve 19 which, when open, permits gas to discharge to the atmosphere through a clearance between the operating rod 20 and the passage therefor in the body portion 10.

OPERATION

The refrigerating instrument described above operates as follows: The surgeon or other operator grips the flask 17 to which heat is transmitted from his hand and this brings it up to a temperature of about 34°C. This causes the refrigerant, which is in a liquid condition in the flask, to evaporate partly, and simultaneously there is a rise in the pressure within the flask 17.

On pressing the trigger 21, the opening of the poppet valve 19, which is located at the downstream end of the circuit, permits fluid in a gaseous state but at about 34°C to flow from the flask 17 towards the probe tip 13 through the conduits 42, 42a and along the annular passageway 31. The fluid then flows back along the annular passageway 30, through conduits 43, 44 to the condenser 24 where it cools to ambient temperature, for instance, 20°C, whereby under the prevailing pressure it liquifies all or in part. Still under the action of the pressure prevailing in the flask the refrigerant reaches the capillary tube 25 through conduit 45. The capillary tube 24 acts as throttle causing a considerably pressure difference between the expansion chamber 34 and the conduit 45. On reaching the end of the capillary tube 25, the refrigerant vigorously expands into the chamber 34 thereby strongly reducing the temperature both of the plate 32 as desired and of the separator 33. The fall in temperature within the chamber 34 is, however, not transmitted to the outermost tube 28 by virtue of the interposed gaseous fluid jacket which acts as a thermal insulator both at the separator 33, and still more at the region further back from the probe tip 13, where the provision of the tube 27 provides a double fluid jacket.

The refrigerant fluid within the fluid jacket enters first along the outer annular passageway 31, so that the fluid, which is in a gaseous condition, is in contact with the tube 28 whilst at its warmest. It is quite possible that the fluid may liquify as it travels along the return conduit 30, ahead of the condenser 24, but this is not objectionable.

After expanding in the chamber 34 the refrigerant which is again in a gaseous state passes to the discharge valve 19 through the annular passageway 29 and the conduit 46 and finally escapes to the atmosphere.

I claim:

1. In a refrigerating apparatus suitable for medical use, of the type comprising:
    a body,
    a tubular probe projecting from said body, said probe comprising,
    a first tube formed as a capillary tube, and connected by one end to a first conduit within said body,
    a second tube surrounding said first tube and connected by one end to a second conduit within said body, the other end of said second tube being closed and forming a chamber around the other end of said first tube and an annular passageway between itself and said first tube,
    a source of refrigerant fluid under pressure,
    means defining a flow path for said refrigerant fluid from said source of refrigerant fluid to said first conduit, and
    a control valve in said second conduit operable to connect said second conduit to the atmosphere whereby to permit refrigerant fluid to flow from said source means along said first tube from which it expands into said chamber at said other end of said second tube to effect refrigeration of the walls of said chamber by flash evaporation and expansion, and to flow from said chamber along said annular passageway through said control valve to the atmosphere,
    the improvement wherein,
    said second tube is surrounded by a third tube which is coaxial therewith and spaced therefrom to define a second annular passageway between said second and third tubes,
    said third tube is surrounded by a fourth tube which is coaxial therewith and spaced therefrom to define a third annular passageway, said second and third annular passageways communicating with one another but not with said expansion chamber at said other end of said probe and said second and third tubes being of such a length that they surround all but a part of said expansion chamber, which is left exposed, and
    means interconnecting said second and third annular passageways in series in the flow path of said refrigerant between said source and said first tube whereby said refrigerant acts as a thermal insulation for said first and second tubes which are in thermal contact with said expansion chamber.

2. The refrigeration apparatus of claim 1, wherein said source of refrigerant under pressure is a container attachable to said body to serve as a handgrip for said apparatus, and wherein said means defining a flow path from said source of refrigerant to said first tube includes a condenser coil carried by said body and a plurality of conduits formed as drillings in said body.

3. A tubular probe for refrigeration apparatus such as refrigeration apparatus for medical use, comprising:
    a first tube formed as a capillary tube through which, in use of the probe, a refrigerant fluid is passed from one end to the other,
    a second tube coaxially surrounding said first tube and closed adjacent said other end of said first tube to define an expansion chamber around said other end of said first tube and a first annular passageway between said first tube and said second tube, a third tube coaxially surrounding said second tube and defining therewith a second annular passageway,
a fourth tube coaxially surrounding said third tube and defining therewith a third annular passageway, said second and third annular passageways communicating with one another adjacent said exapansion chamber but not communicating therewith, and said third and fourth tubes being of such a length that they partly surround said expansion chamber so as to leave a part only thereof exposed.

* * * * *